United States Patent
Nagasaka

(10) Patent No.: US 9,964,604 B2
(45) Date of Patent: May 8, 2018

(54) MAGNETIC FIELD MEASUREMENT METHOD AND MAGNETIC FIELD MEASUREMENT DEVICE FOR MEASURING AND OFFSETTING ORIGINAL MAGNETIC FIELD

(71) Applicant: SEIKO EPSON CORPORATION, Tokyo (JP)

(72) Inventor: Kimio Nagasaka, Hokuto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 146 days.

(21) Appl. No.: 14/928,320

(22) Filed: Oct. 30, 2015

(65) Prior Publication Data
US 2016/0131723 A1 May 12, 2016

(30) Foreign Application Priority Data

Nov. 12, 2014 (JP) .................. 2014-229915
Nov. 12, 2014 (JP) .................. 2014-229916
(Continued)

(51) Int. Cl.
*G01R 33/02* (2006.01)
*G01R 33/032* (2006.01)
(Continued)

(52) U.S. Cl.
CPC ...... *G01R 33/0322* (2013.01); *A61B 5/04007* (2013.01); *A61B 5/04008* (2013.01); *G01R 33/0206* (2013.01); *G01R 33/26* (2013.01)

(58) Field of Classification Search
CPC ...... G01R 33/26; G01R 33/282; G01R 33/28; G01R 33/281; G01R 33/0327;
(Continued)

(56) References Cited

U.S. PATENT DOCUMENTS 5,189,368 A * 2/1993 Chase .................. G01R 33/032
102/417
8,773,120 B2 7/2014 Jager et al.
(Continued)

FOREIGN PATENT DOCUMENTS

JP 2013-015523 A 1/2013
JP 2013-108833 A 6/2013

OTHER PUBLICATIONS

Apr. 6, 2016 Extended European Search Report issued in European Patent Application No. 15193841.2.

*Primary Examiner* — Vinh Nguyen
(74) *Attorney, Agent, or Firm* — Oliff PLC

(57) ABSTRACT

A light source unit irradiates a gas cell disposed in a measurement region with linearly polarized light in which the direction of travel is a z-axis direction and the vibration direction of an electric field is a y-axis direction. A polarimeter detects optical characteristics of light passing through the gas cell. A magnetic field generator applies an artificial magnetic field, capable of varying an x-axis component, a y-axis component, and a z-axis component, to the measurement region. A calculation control unit generates a plurality of artificial magnetic fields, calculates a magnetization value or a value corresponding to the magnetization value on the basis of the detection results of the polarimeter, and calculates an original magnetic field present in the measurement region, using an artificial magnetic field when the magnetization value or the value corresponding to the magnetization value satisfies a condition for external value.

6 Claims, 8 Drawing Sheets

(30) Foreign Application Priority Data

May 27, 2015 (JP) ................................. 2015-107151
May 27, 2015 (JP) ................................. 2015-107152

(51) Int. Cl.
*G01R 33/26* (2006.01)
*A61B 5/04* (2006.01)

(58) Field of Classification Search
CPC ............ G01R 33/0354; G01R 33/0322; G01R 33/1269; G01R 33/1276; G01R 33/0206; G01R 33/0213; G01R 33/022; G01R 33/025; G01R 33/24; G01R 33/323; G01R 33/032; G01R 33/028; G01R 33/0385; G01R 33/0017; G01R 33/0023; G01R 33/0076; G01R 33/302; G01R 33/326; G01R 33/482; G01N 21/1717; G01N 21/4795; G01N 2021/1727; G01N 2021/218; G01N 24/006; G01N 21/45; G01N 2021/399; G01N 2201/0636; G01N 21/35; G01N 21/359; G01N 2015/0693; G01N 2021/1723; G01N 2021/00; G01V 3/082; G02F 2001/133638; G06F 3/0321; H01S 3/08059; H01S 5/02248; H01S 5/0683; H01S 5/141; G01C 19/62; H02S 40/22

See application file for complete search history.

(56) References Cited

U.S. PATENT DOCUMENTS

| | | | |
|---|---|---|---|
| 9,274,182 B2* | 3/2016 | Ueno | .................. G01R 33/032 |
| 9,720,058 B2* | 8/2017 | Ueno | ..................... G01R 33/26 |
| 2014/0247045 A1 | 9/2014 | Kornack et al. | |
| 2015/0214895 A1* | 7/2015 | Hashi | ........................ G04F 5/14 331/94.1 |

* cited by examiner

MAGNETIC FIELD MEASUREMENT METHOD AND MAGNETIC FIELD MEASUREMENT DEVICE FOR MEASURING AND OFFSETTING ORIGINAL MAGNETIC FIELD

CROSS-REFERENCE TO RELATED APPLICATIONS

The present application claims priority to Japanese Patent Applications JP 2014-229915, filed Nov. 12, 2014, JP 2014-229916, filed Nov. 12, 2014, JP 2015-107152, filed May 27, 2015 and JP 2015-107151, filed May 27, 2015, the entire disclosures of which are hereby incorporated by reference.

BACKGROUND

1. Technical Field

Various embodiments of the present invention relate to a magnetic field measurement method of measuring a magnetic field, and the like.

2. Related Art

A device for measuring a weak magnetic field of a magnetic field (biomagnetic field) or the like, such as a magnetic field (magnetocardiogram) from the heart or a magnetic field (magnetoencephalo) from the brain, which is radiated by a living body is known in which an optically-pumped magnetic sensor that irradiates a gas cell having alkali metal atoms sealed therein with linearly polarized light and measures a magnetic field through the rotation of the plane of polarization is used (see, for example, JP-A-2013-108833).

In the measurement of a weak magnetic field using an optically-pumped magnetic sensor, it is necessary to cancel a magnetic field (referred to as an original magnetic field) caused by, for example, an environment of geomagnetism, city noise or the like which is present in a measurement region having a gas cell disposed therein. When the original magnetic field is present, sensitivity to a magnetic field radiated by a measuring object decreases due to the influence thereof, or a decrease in the accuracy of measurement is caused.

SUMMARY

An advantage of some aspects of the invention is to propose a new method of specifying an original magnetic field which is present in a measurement region.

The various embodiments of the invention can be implemented by the following forms or application examples.

APPLICATION EXAMPLE

A magnetic field measurement method according to this application example measures a magnetic field of a measurement region in a magnetic field measurement device including a light source unit that emits linearly polarized light in which a first direction, a second direction and a third direction are orthogonal to each other, a medium, disposed in the measurement region, which changes optical characteristics of the linearly polarized light in accordance with a magnetic field, and which is irradiated along the third direction with the linearly polarized light of which a vibration direction of an electric field is the second direction, an optical detector that detects the optical characteristics, and a magnetic field generator that applies an artificial magnetic field to the measurement region. The method includes: generating a plurality of artificial magnetic fields, obtained by changing an artificial magnetic field component in the third direction, in the magnetic field generator; calculating a magnetization value which is a component of a magnetization vector of the medium in the first direction or a value corresponding to the magnetization value on the basis of detection results of the optical detector; and calculating an original magnetic field present in the measurement region, using an artificial magnetic field when the magnetization value or the value corresponding to the magnetization value satisfies a specified condition.

According to this application example, it is possible to obtain an original magnetic field derived from an environment in the measurement region in which a magnetic field radiated from the measuring object is present.

APPLICATION EXAMPLE

A magnetic field measurement method according to this application example measures a magnetic field of a measurement region in a magnetic field measurement device including a light source unit that emits linearly polarized light in which a first direction, a second direction and a third direction are orthogonal to each other, a medium, disposed in the measurement region, which changes optical characteristics of the linearly polarized light in accordance with a magnetic field, and which is irradiated along the third direction with the linearly polarized light of which a vibration direction of an electric field is the second direction, an optical detector that detects the optical characteristics, and a magnetic field generator that applies an artificial magnetic field to the measurement region. The method includes: generating a plurality of artificial magnetic fields, obtained by changing an artificial magnetic field component in the third direction and one artificial magnetic field component in the first direction and the second direction, in the magnetic field generator, in a state where the other artificial magnetic field component in the first direction and the second direction is set to a fixed value; calculating a magnetization value which is a component of a magnetization vector of the medium in the first direction or a value corresponding to the magnetization value on the basis of detection results of the optical detector; and calculating an original magnetic field present in the measurement region, using an artificial magnetic field when the magnetization value satisfies a condition for external value.

According to this application example, it is possible to obtain an original magnetic field derived from an environment in the measurement region in which a magnetic field radiated from the measuring object is present.

In the magnetic field measurement method according to the application example, it is preferable that the calculating of the original magnetic field includes calculating using a first magnetic field which is an artificial magnetic field when the magnetization value or value corresponding to the magnetization value satisfies a maximum value condition, and a second magnetic field which is an artificial magnetic field when the magnetization value or value corresponding to the magnetization value satisfies a minimum value condition.

According to this method, it is possible to accurately obtain an original magnetic field.

In the magnetic field measurement method according to the application example, the one artificial magnetic field component may be an artificial magnetic field component in the second direction, and the other artificial magnetic field component may be an artificial magnetic field component in the first direction, and the calculating of the original magnetic field may include calculating using the following Expressions (1) to (3).

$$C_x = -\frac{A_{px} + A_{vx}}{2} \quad (1)$$

$$C_y = \frac{A_{px} - A_{vx}}{2} - A_{fy} \quad (2)$$

$$C_z = -\frac{A_{pz} + A_{vz}}{2} \quad (3)$$

where, $A_{px}$ is a component of the first magnetic field in the first direction, $A_{vx}$ is a component of the second magnetic field in the first direction, $A_{pz}$ is a component of the first magnetic field in the third direction, $A_{vz}$ is a component of the second magnetic field in the third direction, $A_{fy}$ is the fixed value, $C_x$ is a component of the original magnetic field in the first direction, $C_y$ is a component of the original magnetic field in the second direction, and $C_z$ is a component of the original magnetic field in the third direction.

In the magnetic field measurement method according to the application example, the one artificial magnetic field component may be an artificial magnetic field component in the first direction, and the other artificial magnetic field component may be an artificial magnetic field component in the second direction, and the calculating of the original magnetic field may include calculating using the following Expressions (4) to (6).

$$C_x = -\frac{A_{py} + A_{vy}}{2} - A_{fx} \quad (4)$$

$$C_y = \frac{A_{py} - A_{vy}}{2} \quad (5)$$

$$C_z = -\frac{A_{pz} + A_{vz}}{2} \quad (6)$$

where, $A_{py}$ is a component of the first magnetic field in the second direction, $A_{vy}$ is a component of the second magnetic field in the second direction, $A_{pz}$ is a component of the first magnetic field in the third direction, $A_{vz}$ is a component of the second magnetic field in the third direction, $A_{fx}$ is the fixed value, $C_x$ is a component of the original magnetic field in the first direction, $C_y$ is a component of the original magnetic field in the second direction, and $C_z$ is a component of the original magnetic field in the third direction.

According to these methods, it is possible to more accurately obtain an original magnetic field.

In the magnetic field measurement method according to the application example, it is preferable that the fixed value is zero.

According to this method, the above expressions are simplified by setting the artificial magnetic field component to zero in the first direction or the second direction, and thus it is possible to more simply obtain an original magnetic field.

APPLICATION EXAMPLE

A magnetic field measurement method according to this application example measures a magnetic field of a measurement region in a magnetic field measurement device including a light source unit that emits linearly polarized light in which a first direction, a second direction and a third direction are orthogonal to each other, a medium, disposed in the measurement region, which changes optical characteristics of the linearly polarized light in accordance with a magnetic field, and which is irradiated along the third direction with the linearly polarized light of which a vibration direction of an electric field is the second direction, an optical detector that detects the optical characteristics, and a magnetic field generator that applies an artificial magnetic field to the measurement region. The method includes: generating artificial magnetic fields of a plurality of combinations obtained by changing artificial magnetic field components in the first direction to the third direction, that is, artificial magnetic fields obtained by periodically changing the artificial magnetic field component in the third direction, in the magnetic field generator; calculating a magnetization value which is a component of a magnetization vector of the medium in the first direction or a value corresponding to the magnetization value on the basis of detection results of the optical detector; and calculating an original magnetic field present in the measurement region, using an artificial magnetic field when a ratio of a temporal change of the magnetization value or value corresponding to the magnetization value to a temporal change of the artificial magnetic field component in the third direction satisfies a condition for external value.

According to this application example, it is possible to obtain an original magnetic field derived from an environment in the measurement region in which a magnetic field radiated from the measuring object is present.

In the magnetic field measurement method according to the application example, it is preferable that the calculating of the original magnetic field is based on the magnetic field of the measurement region when the condition for external value is satisfied being a zero magnetic field.

According to this method, it is possible to accurately obtain an original magnetic field.

In the magnetic field measurement method according to the application example, it is preferable that the artificial magnetic field component in the third direction includes a change at a period equal to or less than a cut-off angular frequency.

According to this method, it is possible to simply and accurately obtain an original magnetic field.

In the magnetic field measurement method according to the application example, it is preferable that the magnetic field measurement method further includes generating a magnetic field of a difference in the original magnetic field with respect to a target magnetic field, in the magnetic field generator, disposing a measuring object in the measurement region, and measuring a magnetic field which is radiated by the measuring object, using the detection results of the optical detector while the magnetic field of the difference is generated.

According to this method, it is possible to accurately measure a magnetic field radiated by the measuring object by offsetting an influence of the original magnetic field in the measurement region.

APPLICATION EXAMPLE

A magnetic field measurement device according to this application example includes: a light source unit that emits linearly polarized light in which a first direction, a second direction and a third direction are orthogonal to each other; a medium, disposed in a measurement region, which changes optical characteristics in accordance with a magnetic field, which is irradiated from the third direction with the linearly polarized light of which a vibration direction of an electric field is the second direction, and which transmits the irradiation linearly polarized light; an optical detector that detects the optical characteristics; a magnetic field generator that applies an artificial magnetic field, capable of varying each component in the first direction, the second direction, and the third direction, to the measurement region; and a calculation control unit that executes generating a plurality of artificial magnetic fields, obtained by changing an artificial magnetic field component in the third direction and one artificial magnetic field component in the first direction and the second direction, in the magnetic field generator, in a state where the other artificial magnetic field component in the first direction and the second direction is set to a fixed value, calculating a magnetization value which is a component of a magnetization vector of the medium in the first direction or a value corresponding to the magnetization value on the basis of detection results of the optical detector, and calculating an original magnetic field present in the measurement region, using the artificial magnetic field of the magnetic field generator when the magnetization value or value corresponding to the magnetization value satisfies a condition for external value.

APPLICATION EXAMPLE

A magnetic field measurement device according to this application example includes: a light source unit that emits linearly polarized light in which a first direction, a second direction and a third direction are orthogonal to each other; a medium, disposed in a measurement region, which changes optical characteristics in accordance with a magnetic field, which is irradiated from the third direction with the linearly polarized light of which a vibration direction of an electric field is the second direction, and which transmits the irradiation linearly polarized light; an optical detector that detects the optical characteristics; a magnetic field generator that applies an artificial magnetic field, capable of varying each component in the first direction, the second direction, and the third direction, to the measurement region; and a calculation control unit executes generating artificial magnetic fields of a plurality of combinations obtained by changing artificial magnetic field components in the first direction to the third direction, that is, artificial magnetic fields obtained by periodically changing the artificial magnetic field component in the third direction, in the magnetic field generator, calculating a magnetization value which is a component of a magnetization vector of the medium in the first direction or a value corresponding to the magnetization value on the basis of detection results of the optical detector, and calculating an original magnetic field present in the measurement region, using an artificial magnetic field when a ratio of a temporal change of the magnetization value or value corresponding to the magnetization value to a temporal change of the artificial magnetic field component in the third direction satisfies a condition for external value.

According to these application examples, it is possible to provide a magnetic field measurement device capable of obtaining an original magnetic field derived from an environment in the measurement region in which a magnetic field radiated from the measuring object is present.

BRIEF DESCRIPTION OF THE DRAWINGS

Various embodiments of the invention will be described with reference to the accompanying drawings, wherein like numbers reference like elements.

DETAILED DESCRIPTION

Figure 1:
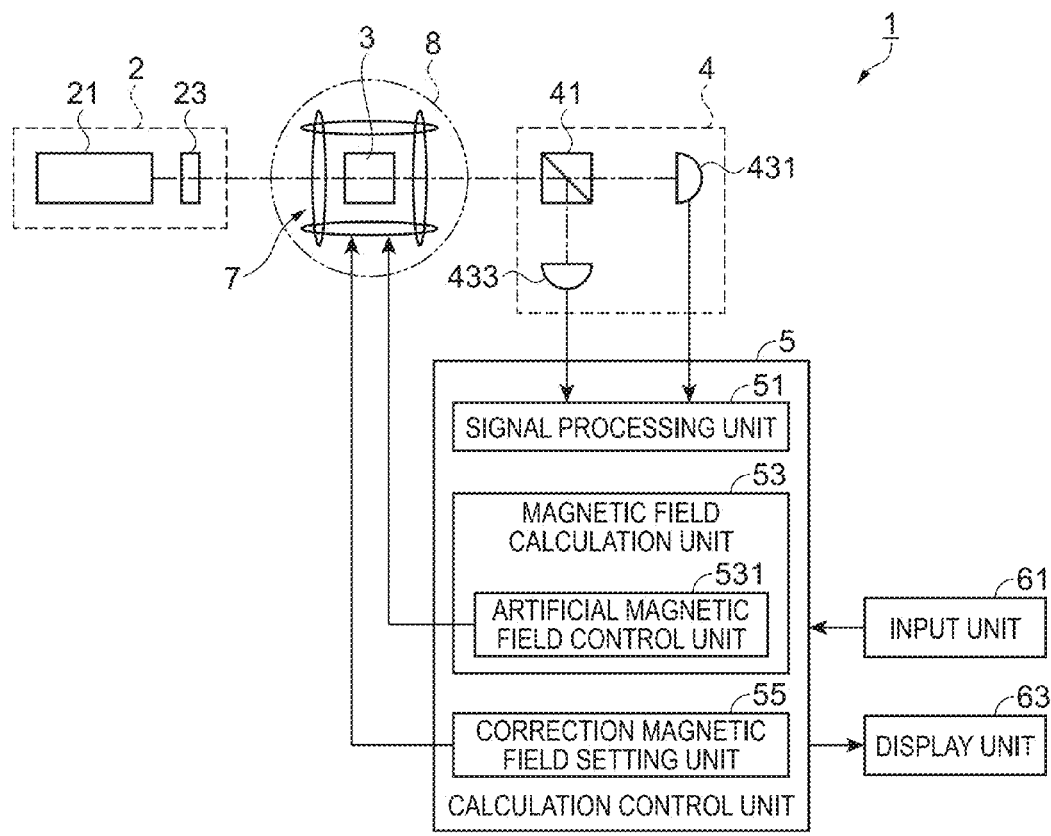
FIG. 1 is a diagram illustrating an entire configuration example of a magnetic field measurement device according to Embodiment 1.

Hereinafter, one form for implementing a magnetic field measurement method and a magnetic field measurement device according to various embodiments of the invention will be described. Meanwhile, the invention is not limited by embodiments described below, and forms capable of applying the invention are not limited to the following embodiments. In addition, in the accompanying drawings, the same components are denoted by the same reference numerals and signs.

Embodiment 1
Entire Configuration

Figure 2:
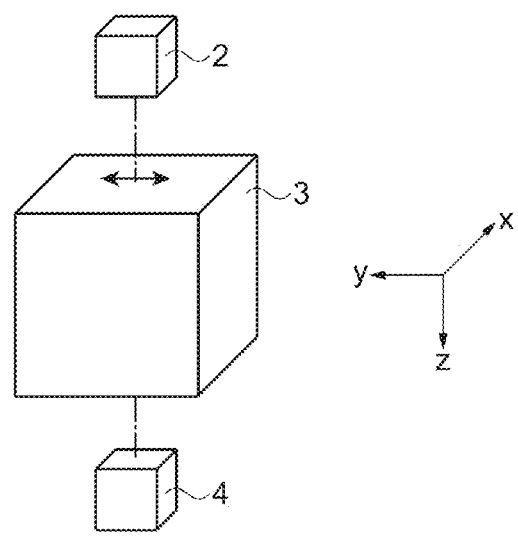
FIG. 2 is a diagram illustrating an outline of an arrangement relation between a light source unit, a gas cell, and a polarimeter.

FIG. 1 is a diagram illustrating an entire configuration example of a magnetic field measurement device 1 of the present embodiment. In addition, FIG. 2 is a diagram illustrating an outline of an arrangement relation between a light source unit 2, a gas cell 3, and a polarimeter 4 constituting the magnetic field measurement device 1. The magnetic field measurement device 1 of the present embodiment is used in a magnetocardiograph that measures a magnetocardiogram or a magnetoencephalography that measures a magnetoencephalo. The magnetic field measurement device 1 has a so-called one-beam-type magnetic sensor incorporated therein which uses both pump light irradiation and probe light irradiation, as an optically-pumped magnetic sensor, and measures a magnetic field using nonlinear magneto-optical rotation (NMOR). Meanwhile, without being limited to a one-beam type, a so-called two-beam-type configuration may be used in which a light source unit that performs irradiation with pump light and a light source unit that performs irradiation with probe light are separated from each other.

As shown in FIG. 1, the magnetic field measurement device 1 includes the light source unit 2, the gas cell 3, the polarimeter 4 as an optical detector, a calculation control unit 5, and a magnetic field generator 7. In the present embodiment, as shown in FIG. 2, a third direction which is the direction of travel of linearly polarized light (irradiation light) in which irradiation with both the pump light and the probe light is performed by the light source unit 2 is defined as a z-axis direction, a second direction which is the vibration direction of a electric field of the linearly polarized light is defined as a y-axis direction, and a first direction perpendicular to the z-axis direction and the y-axis direction is defined as an x-axis direction. A space in which the light source unit 2, the gas cell 3, and the polarimeter 4 are disposed is denoted as an orthogonal three-axis xyz coordinate space.

The light source unit 2 is constituted by a light source 21 and a polarizing plate 23, and emits linearly polarized light that propagates in the z-axis direction and vibrates along the y-axis direction, as irradiation light. The light source 21 is a laser generating device that generates a laser beam having a frequency corresponding to the transition of a hyperfine structure level of gaseous atoms sealed in the gas cell 3. Specifically, the wavelength of a laser beam is a wavelength equivalent to state transition between hyperfine structure quantum numbers F and F' (=F−1) of a line D1 of gaseous atoms (such as, for example, cesium, potassium, or rubidium) within the gas cell 3. The polarizing plate 23 is an element that polarizes a laser beam from the light source 21 in a predetermined direction and forms linearly polarized light. The irradiation light emitted from the light source unit 2 is guided by, for example, an optical fiber or the like, and the gas cell 3 is irradiated therewith.

The gas cell 3 is an element made of glass in which alkali metal atoms such as potassium (K), rubidium (Rb), or cesium (Cs) are sealed in a gaseous state. The alkali metal atoms are excited (optically pumped) by the irradiation light (pump light and probe light) from the light source unit 2, and has a property as a medium for rotating the plane of polarization of light passing through the gas cell 3 in accordance with the intensity of a magnetic field. The gas cell 3 is disposed inside a magnetic shield 8 shown by a dashed-two dotted line in FIG. 1. The magnetic shield 8 is used for shielding above a certain magnetism and forming a space in which magnetism is reduced as compared to the outside of the magnetic shield 8, and the area of a subject to be tested as a measuring object such as the heart or the brain is located at a measurement region (peripheral region of the gas cell 3) in which the gas cell 3 is disposed inside the magnetic shield 8 during measurement. As described later, the measurement region can be set to a target magnetic field (for example, zero magnetic field) by the magnetic field generator 7 installed within the magnetic shield 8. The magnetic field measurement device 1 sets the magnetic field of a measurement region to be in a state of the target magnetic field, and then disposes the measurement area of a subject to be tested in the measurement region, to thereby measure a magnetic field which is radiated by the measurement area. Therefore, it can be also said that a magnetic field forming device is included in the magnetic field measurement device 1. Meanwhile, the gaseous atoms within the gas cell 3 may be set to be in a gaseous state during the measurement of a magnetic field, and may be set to be in a gaseous state at all times. In addition, the material of the gas cell 3 may be a material that transmits the irradiation light without being limited to glass, and may be a resin or the like.

The polarimeter 4 is constituted by a polarization splitter 41 and two photodetectors 431 and 433, and is configured to split the irradiation light (probe light) passing through the gas cell 3 into two polarization components perpendicular to each other and detect each light intensity. The polarization splitter 41 is an element that splits the irradiation light from the gas cell 3 into components of an α-axis and a β-axis (see FIG. 3) perpendicular to each other in each axial direction. One polarization component which is split is guided to the photodetector 431, and the other polarization component is guided to the photodetector 433. The polarization splitter 41 is constituted by, for example, a Wollaston prism, a polarization beam splitter or the like. The photodetectors 431 and 433 receives the polarization components split by the polarization splitter 41, generates signals based on the amount of light received, and outputs the signals to a signal processing unit 51 of the calculation control unit 5.

The calculation control unit 5 is configured using a microprocessor such as a CPU (Central Processing Unit), an ASIC (Application Specific Integrated Circuit), an IC (Integrated Circuit) memory, or the like, and controls an operation of each unit of the device as a whole. The calculation control unit 5 includes the signal processing unit 51, a magnetic field calculation unit 53, and a correction magnetic field setting unit 55, and performs magnetic field measurement in the measurement region, a magnetic field forming process (see FIG. 10) for forming a target magnetic field (for example, zero magnetic field) in the measurement region, or the like. In addition, the calculation control unit 5 includes a storage unit such as flash memory or a hard disk, and readably stores a program in the storage unit when the magnetic field forming process is realized by executing the program.

In addition, an input unit 61 for inputting required information and a display unit 63 for displaying measurement results of a magnetic field or the like are appropriately connected to the calculation control unit 5. The input unit 61 is constituted by input devices of various types of switch such as a button switch, a lever switch, or a dial switch, a touch panel, a keyboard, a mouse, and the like. The display unit 63 is constituted by a display device such as an LCD (Liquid Crystal Display) or an EL display (Electroluminescence display).

The signal processing unit 51 measures the magnetic field of the measurement region by calculating the rotation angle of the plane of polarization which is rotated by the probe light passing through the gas cell 3. The signal processing unit 51 processes signals from the photodetectors 431 and 433, and calculates a square sum $W_+$ and a square difference $W_-$ of the components of the α-axis and the β-axis in each axial direction in accordance with the following Expressions (7) and (8). $E_α$ indicates the light intensity of the component in an α-axis direction, and $E_β$ indicates the light intensity of the component in a β-axis direction.

$$W_+ = E_α^2 + E_β^2 \tag{7}$$

$$W_- = E_α^2 - E_β^2 \tag{8}$$

The magnetic field calculation unit 53 calculates a magnetic field present in the measurement region, using the value of an artificial magnetic field when the square difference W_ calculated by the signal processing unit 51 satisfies specified conditions such as a maximum value condition and a minimum value condition described later as a condition for external value. The magnetic field calculation unit 53 includes an artificial magnetic field control unit 531. The artificial magnetic field control unit 531 applies an artificial magnetic field to the measurement region by controlling the magnetic field generator 7, and the magnetic field calculation unit 53 measures a spin polarization degree $M_x$ in that case. For example, during the measurement of a magnetic field (referred to as an original magnetic field) present in the measurement region when the artificial magnetic field is set to zero, in a state where an artificial magnetic field component (referred to as a y-axis component) in the y-axis direction is set to a fixed value (predetermined value), a plurality of artificial magnetic fields obtained by changing a artificial magnetic field component (referred to as an x-axis component) in the x-axis direction and a artificial magnetic field component (referred to as a z-axis component) in the z-axis direction are sequentially generated in the measurement region, and in a state where one artificial magnetic field is applied, the spin polarization degree $M_x$ in that case is measured. In short, a first artificial magnetic field is generated, and the spin polarization degree $M_x$ when the first artificial magnetic field is applied is measured. Similarly, a second artificial magnetic field is generated, and the spin polarization degree $M_x$ when the second artificial magnetic field is applied is measured. Hereinafter, by repeating the same process, an N-th artificial magnetic field is generated (N is an integer equal to or greater than 2), and the spin polarization degree $M_x$ when the N-th artificial magnetic field is applied is measured. In the first artificial magnetic field to the N-th artificial magnetic field, the y-axis component is a fixed value and is common, but the x-axis component and the z-axis component are scanned, and the spin polarization degree $M_x$ is measured in each state. Meanwhile, the original magnetic field is typically an external magnetic field entering the magnetic shield 8 from the outside, but the original magnetic field itself may be present in a magnetic field to be measured, for example, such as magnetocardiogram or magnetoencephalo which is radiated by a living body.

The correction magnetic field setting unit 55 sets a correction magnetic field for correcting the original magnetic field calculated by the magnetic field calculation unit 53, and forms a target magnetic field in the measurement region by controlling the magnetic field generator 7 to generate the correction magnetic field in the measurement region. When the original magnetic field is an external magnetic field, an example of correction of the original magnetic field is to offset the original magnetic field, and set the target magnetic field to a zero magnetic field.

The magnetic field generator 7 is constituted by a three-axis Helmholtz coil for applying magnetic fields of the x-axis, the y-axis, and the z-axis in each axial direction, and includes a pair of coils disposed in pairs in each axial direction with the gas cell 3 interposed therebetween within the magnetic shield 8, and a current supply portion that supplies a current to these coils. The magnetic field generator 7 can generate a magnetic field in any three-dimensional direction in the measurement region.

Meanwhile, the z-axis direction is a third direction in embodiments of the invention, but as shown in FIG. 2, the irradiation light (pump light) is not necessarily limited to be emitted from the light source unit 2 in the z-axis direction. The irradiation light (pump light) may be incident on the gas cell 3 in the z-axis direction after emission.

Principle

In the magnetic field measurement device 1 configured in this manner, when the gas cell 3 is irradiated with the pump light from the light source unit 2, gaseous atoms within the gas cell 3 are spin-polarized. The probability distribution of magnetic moments generated by this spin polarization when energy transitions from the hyperfine structure quantum number F to F' (=F−1) forms an ellipsoidal shape extending along the y-axis direction which is the vibration direction of the linearly polarized light. This biased probability distribution is referred to as "alignment", and generating the alignment is referred to as "optical pumping". When the measurement region is a zero magnetic field, the generated alignment remains along the y-axis direction which is the vibration direction of the pump light. However, when a magnetic field which is not zero is present in the measurement region, the alignment performs a precessional motion using the direction of a magnetic field as a rotational axis. As a result, the plane of polarization of the linearly polarized light rotates at an angle based on the magnetic field of the measurement region, using the z-axis direction which is the direction of travel as a rotational axis.

Figure 3:
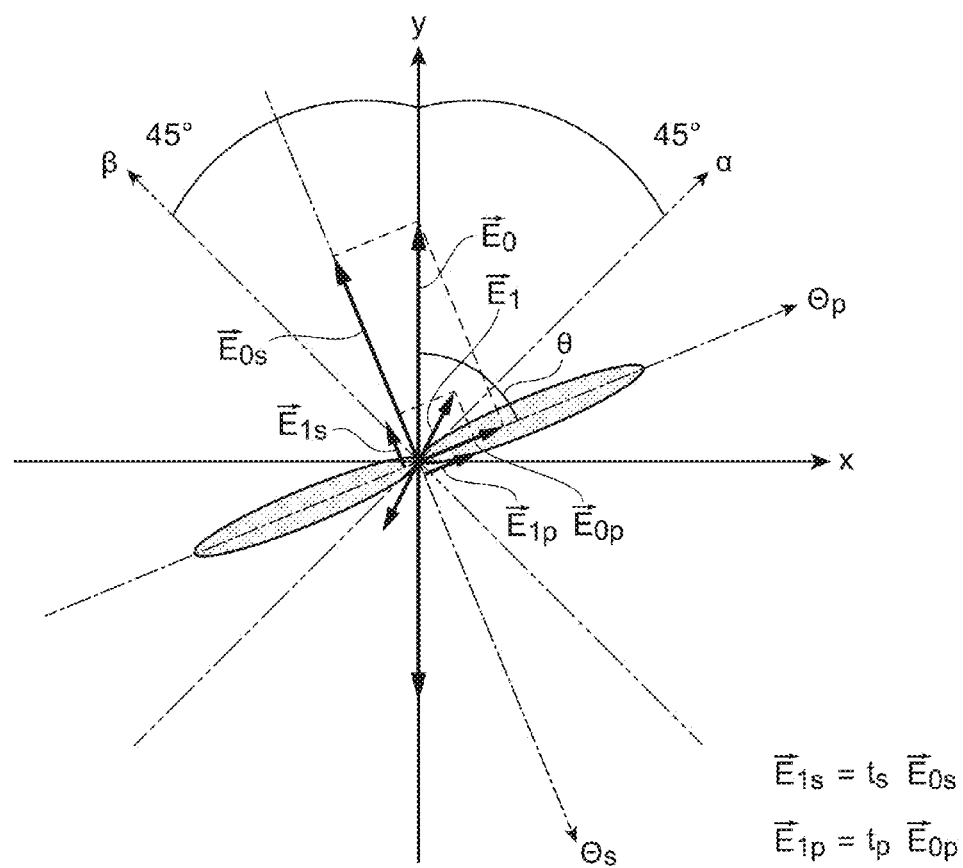
FIG. 3 is a diagram illustrating a rotation of the plane of polarization.

FIG. 3 is a diagram illustrating a rotation of the plane of polarization. As described above, the alignment performs a precessional motion in accordance with the magnetic field (magnetic field received by the gas cell 3) of the measurement region. An optical pumping action caused by the pump light and a relaxation action caused by the collision or the like of the gaseous atoms with the inner wall of the gas cell 3 are applied, and thus the alignment is set to be in a steady state in an arrangement in which the alignment is rotated by an angle (θ) based on the intensity of a magnetic field with respect to the y-axis, as shown in an ellipsoidal body hatched in FIG. 3.

The probe light passing through the gas cell 3 receives an action of linear dichroism due to this alignment. The linear dichroism refers to a property in which transmissivities of the linearly polarized light different from each other a direction (direction of $\Theta_p$) along the alignment and a direction (direction of $\Theta_s$) perpendicular to the alignment. Specifically, since larger components in the direction perpendicular to the alignment are absorbed than those in the direction along the alignment, the plane of polarization of the probe light is rotated so as to approach the direction along the alignment.

For example, in the present embodiment, the probe light incident on the gas cell 3 is linearly polarized light of a vector $E_0$ in which the vibration direction of an electric field is the y-axis direction. Due to the alignment, an component of the probe light in a $\Theta_p$ direction passes through the gas cell 3 at transmissivity $t_p$, and an component in a $\Theta_s$ direction passes through the gas cell 3 at transmissivity $t_s$. Since the relation of $t_p > t_s$ is established due to the linear dichroism, the vibration direction of an electric field of the probe light passing through the gas cell 3 is set to a vector $E_1$. That is, the plane of polarization of the probe light passing through the gas cell 3 is rotated so as to approach the $\Theta_p$ direction. Specifically, when a vector of a component along the alignment of the vector $E_0$ is denoted by $E_{0P}$, a vector of a component along a direction perpendicular to the alignment of the vector $E_0$ and the direction of travel of the linearly polarized light is denoted by $E_{0S}$ a vector of a component along of the alignment of the vector $E_1$ is denoted by $E_{1P}$, and a vector of a component along a direction perpendicular to the alignment of the vector $E_1$ and the direction of travel of the linearly polarized light is denoted by $E_{1s}$, a relationship between $E_{1P}=t_p \times E_{0P}$ and $E_{1s}=t_s \times E_{0s}$ is established.

As shown in FIG. 3, when an angle (hereinafter, referred to as an "alignment orientation angle") formed by the direction ($\Theta_p$ direction) along the alignment and the vibration direction (vector $E_0$ direction) of an electric field of the probe light incident on the gas cell 3 is set to $\theta$, each component of the vector $E_1$ in the $\Theta_p$ direction and the $\Theta_s$ direction is calculated by the following Expression (9) from the above-mentioned relation, and each component of $(\alpha,\beta)$ in a coordinate system is calculated by the following Expression (10).

$$\vec{E}_1 = (0 \; E_0) \begin{pmatrix} \cos\theta & \sin\theta \\ -\sin\theta & \cos\theta \end{pmatrix} \begin{pmatrix} t_s & 0 \\ 0 & t_p \end{pmatrix} \quad (9)$$

$$(E_\alpha \; E_\beta) = \vec{E}_1 \begin{pmatrix} \cos\left(-\frac{\pi}{4}-\theta\right) & \sin\left(-\frac{\pi}{4}-\theta\right) \\ -\sin\left(-\frac{\pi}{4}-\theta\right) & \cos\left(-\frac{\pi}{4}-\theta\right) \end{pmatrix} \quad (10)$$

Figure 4:
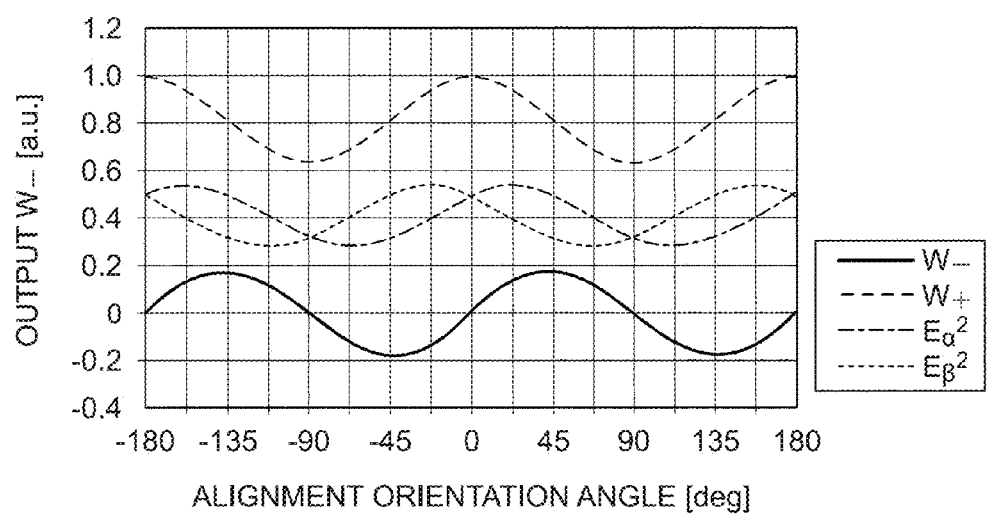
FIG. 4 is a diagram illustrating a relationship between alignment orientation angles and detection results of probe light.

FIG. 4 is a diagram illustrating a relationship between the alignment orientation angle $\theta$ and the detection result of the probe light. In FIG. 4, when focused on the value of the square difference $W_-$, the square difference $W_-$ vibrates using 180 degrees as a period with respect to the alignment orientation angle $\theta$. In the square difference $W_-$, the alignment orientation angle $\theta$ substantially linearly changes with respect to the alignment orientation angle $\theta$ in the range of −45 degrees to +45 degrees, and thus high sensitivity is obtained. In addition, since the center of the linear change is 0 degrees, and the range of the linear change is wider than others (square sum $W_+$ and the like), it is suitable to measure a magnetic field which is generated in the measurement region.

A biomagnetic field such as magnetocardiogram or magnetoencephalo is weak, and the alignment orientation angle $\theta$ is small, and thus the rotation angle of the plane of polarization can be observed with high sensitivity when the square difference $W_-$ is used. However, when an external magnetic field is present in the measurement region, as described above, sensitivity decreases due to the influence, and a decrease in the accuracy of measurement is caused. Generally, the measurement of a magnetic field to be measured such as magnetocardiogram or magnetoencephalo is performed under the environment where the infiltration of a magnetic field (external magnetic field) from the outside to the measurement region is suppressed by the magnetic shield 8 (state where the infiltration of an external magnetic field is low), but it is difficult to sufficiently reduce the external magnetic field to an extent of not influencing measurement through the magnetic shield 8, and thus the original magnetic field (that is, external magnetic field entering the measurement region) may be present in the measurement region. In other words, the infiltration of the external magnetic field is not able to be completely shielded by the magnetic shield 8, and thus the original magnetic field which is not zero may be present in the measurement region. A magnetic shield device capable of shielding magnetism completely is large in size, is expensive in cost, and is high in installation cost or operating cost. Consequently, in the present embodiment, the magnetic shield 8 is used, the original magnetic field within the magnetic shield 8 is then measured, and a magnetic field to be measured is measured in a state where the original magnetic field is reduced by the magnetic field generator 7. However, when the external magnetic field is originally low (when the external magnetic field and the original magnetic field are equal to each other and are small) or when the external magnetic field is stabilized, it is also possible to configure the present embodiment without using the magnetic shield 8.

Since the square difference $W_-$ is substantially proportional to the value of an x-axis component $M_x$ (hereinafter, denoted by the "spin polarization degree $M_x$") of spin polarization degrees ($M_x$, $M_y$, $M_z$) of the alignment generated within the gas cell 3, the spin polarization degree $M_x$ is measured from the output value of the square difference $W_-$. The spin polarization degrees ($M_x$, $M_y$, $M_z$) are equivalent to the magnetization vector of a medium (gas of alkali metal atoms) within the gas cell 3. That is, the square difference $W_-$ is an example of a value corresponding to a magnetization value. Hereinafter, it is examined how the magnetization value (spin polarization degree $M_x$) is changed by a change in the x-axis component, the y-axis component, and the z-axis component (absolute magnetic flux densities $B_x$, $B_y$, and $B_z$) of the magnetic field of the measurement region, using the spin polarization degree $M_x$ as a magnetization value indicating an component (x-axis component) of the magnetization vector in the first direction.

The temporal development of the spin polarization degrees ($M_x$, $M_y$, $M_z$) of the alignment generated by optical pumping is approximated by Bloch equations represented by the following Expressions (11) to (13). Here, $\gamma_F$ indicates a gyromagnetic ratio which is determined by the type of medium gas (alkali metal atom gas) within the gas cell 3. In addition, $\Gamma_0$ indicates a relaxation rate of the spin polarization degrees ($M_x$, $M_y$, $M_z$), and $\Gamma_p$ indicates an optical pumping rate. The relaxation rate $\Gamma_0$ of the spin polarization degree and the optical pumping rate $\Gamma_p$ are represented by the same unit system as that of an angular frequency, and specifically have a unit of radian per second (rad/s). Alternatively, a cut-off angular frequency $\omega_C$ is a sum of the relaxation rate $\Gamma_0$ of the spin polarization degree and the optical pumping rate $\Gamma_p$ ($\omega_C = \Gamma_0 + \Gamma_p$).

$$\frac{dM_x}{dt} = \gamma_F(M_y B_z - M_z B_y) - \Gamma_0 M_x - \Gamma_p M_x \quad (11)$$

$$\frac{dM_y}{dt} = \gamma_F(M_z B_x - M_x B_z) - \Gamma_0 M_y - \Gamma_p(M_p - M_y) \quad (12)$$

$$\frac{dM_z}{dt} = \gamma_F(M_x B_y - M_y B_x) - \Gamma_0 M_z - \Gamma_p M_z \quad (13)$$

Since the gas cell 3 is irradiated with the pump light and the probe light with steadily constant power, steady solutions of the spin polarization degrees ($M_x$, $M_y$, $M_z$) can be solved by setting the left-hand sides of Expressions (11) to (13) to zero. The solutions are represented by the following Expression (14) to (17).

$$M_x = \left(\frac{c}{a}\right)\frac{B_x B_y + a B_z}{a^2 + B_x^2 + B_y^2 + B_z^2} \quad (14)$$

$$M_y = \left(\frac{c}{a}\right)\frac{a^2 + B_y^2}{a^2 + B_x^2 + B_y^2 + B_z^2} \quad (15)$$

$$M_z = \left(\frac{c}{a}\right)\frac{B_y B_z - a B_x}{a^2 + B_x^2 + B_y^2 + B_z^2} \quad (16)$$

$$a = \frac{\Gamma_0 + \Gamma_p}{\gamma_F} \quad c = \Gamma_p M_p \tag{17}$$

Figure 5:
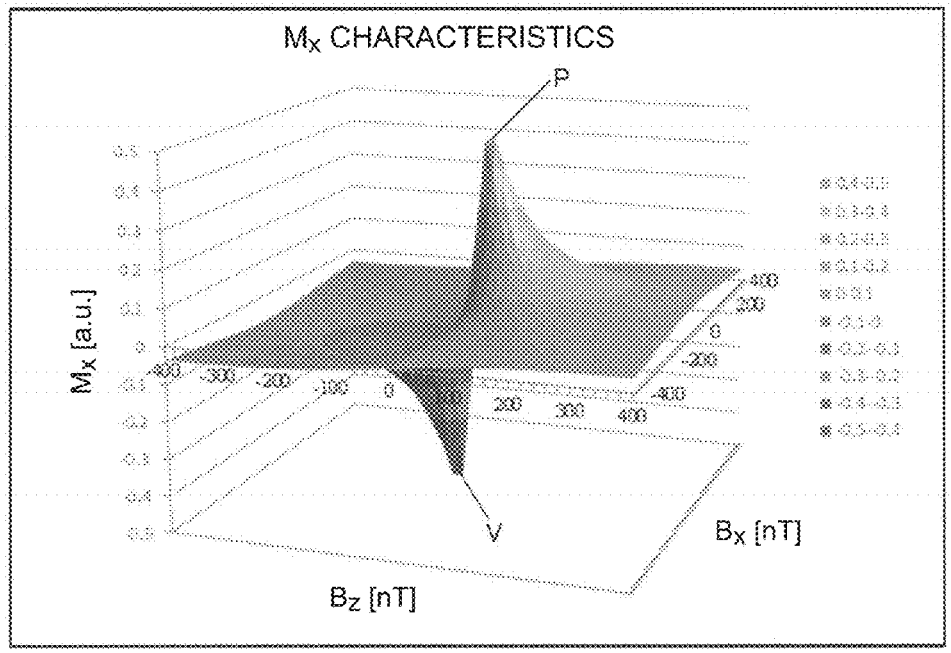
FIG. 5 is a diagram illustrating a distribution of spin polarization degrees $M_x$.
Figure 6:
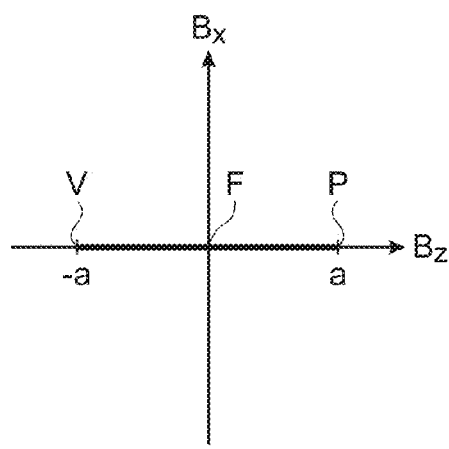
FIG. 6 is a diagram illustrating a positional relationship between a maximum point and a minimum point of the distribution of FIG. 5 in a plane $B_x$–$B_z$.

First, FIG. 5 shows a distribution of the spin polarization degree $M_x$ in which the value of $B_y$ which is the y-axis component of the magnetic field of the measurement region is fixed to $B_y=0$ [nT], and which is obtained by Expression (14) while changing the respective values of $B_x$ which is the x-axis component and $B_z$ which is the z-axis component. As shown in FIG. 5, a maximum point P and a minimum point V appear one by one in the distribution of the spin polarization degree $M_x$. In addition, FIG. 6 is a diagram illustrating a positional relationship between the maximum point P and the minimum point V shown in FIG. 5 in a plane $B_x$-$B_z$. As shown in FIG. 6, a straight line that links the maximum point P to the minimum point V is parallel to a $B_z$ axis when the plane $B_x$-$B_z$ is seen in plan view, and a midpoint F between the respective points P and V passes through the origin of the plane $B_x$-$B_z$.

Figure 7:
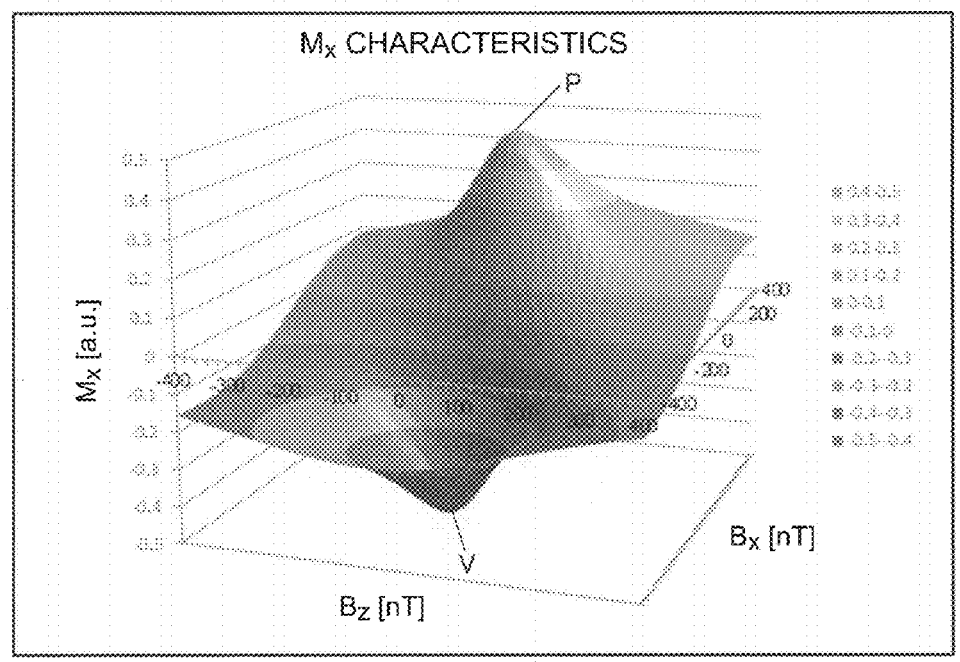
FIG. 7 is another diagram illustrating a distribution of spin polarization degrees $M_x$.
Figure 8:
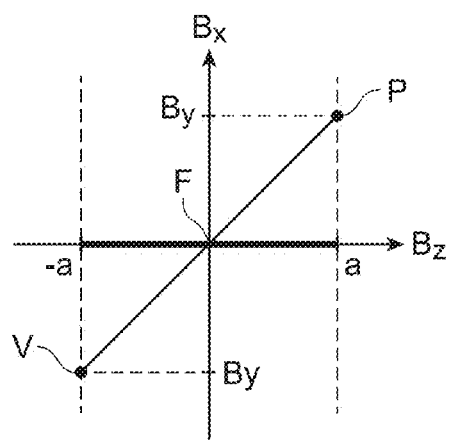
FIG. 8 is a diagram illustrating a positional relationship a maximum point and a minimum point of the distribution of FIG. 7 in a plane $B_x$–$B_z$.

Next, FIG. 7 shows a distribution of the spin polarization degree $M_x$ in which the value of $B_y$ which is the y-axis component of the magnetic field of the measurement region is fixed to $B_y=100$ [nT], and which is obtained while changing the respective values of $B_x$ and $B_z$ in the same way as in FIG. 5. In addition, FIG. 8 is a diagram illustrating a positional relationship between a maximum point P and a minimum point V of the distribution of the spin polarization degree $M_x$ shown in FIG. 7 in the plane $B_x$-$B_z$. As shown in FIG. 8, when the value of $B_y$ is 100 [nT], a straight line that links the maximum point P to the minimum point V is inclined with respect to the $B_z$ axis, but a characteristic in which the midpoint F between the respective points P and V passes through the origin of the plane $B_x$-$B_z$ is not different from the case of $B_y=0$ [nT] shown in FIG. 5.

When $B_y$ is any fixed value $B_f$ ($B_y=B_f$), a magnetic field $P=(P_x, P_y, P_z)$ in which the spin polarization degree $M_x$ is set to the maximum point P and a magnetic field $V=(V_x, V_y, V_z)$ in which the spin polarization degree $M_x$ is set to a minimum point V are obtained by differentiating $M_x$ of Expression (14) by $B_x$, and solving each value obtained by differentiating $M_x$ of Expression (14) by $B_z$ in terms of $B_x$ and $B_z$, setting each value to zero (the following Expression (18)).

$$\frac{\partial M_x}{\partial B_x} = 0 \quad \frac{\partial M_x}{\partial B_z} = 0 \tag{18}$$

The solutions are represented by the following Expressions (19) and (20), and can be obtained from the value of $B_y$ and a constant a shown in Expression (17). Here, a is a constant relating to relaxation.

$$\vec{P} = (P_x, P_y, P_z) = (B_y, B_y, a) = (B_f B_f a) \tag{19}$$

$$\vec{V} = (V_x, V_y, V_z) = (-B_y, B_y, -a) = (-B_f B_f -a) \tag{20}$$

In addition, as shown in the following Expression (21), the midpoint F between the respective points P and V indicated by the solutions of Expressions (19) and (20) constantly satisfies the relation of $B_x=B_z=0$ regardless of the value of $B_y$. meanwhile, in a case of $B_y=B_f=0$, the midpoint F is constantly coincident with the origin.

$$\vec{F} = \frac{\vec{P}+\vec{V}}{2} = \left(\frac{B_y - B_y}{2} \ B_y \ \frac{a-a}{2}\right) = (0 \ B_f \ 0) \tag{21}$$

Consequently, in the magnetic field forming process of the present embodiment, the magnetic field of the measurement region, that is, the magnetization value (spin polarization degree $M_x$) is measured while the magnetic field generator 7 generates a plurality of artificial magnetic fields A obtained by changing the x-axis component ($A_x$) and the z-axis component ($A_z$), in a state where the y-axis component is first set to a fixed value ($A_y=A_{fy}$), on the basis of the characteristics (that is, characteristics of the square difference $W_-$) of the spin polarization degree $M_x$ described above. Specifically, the signal processing unit 51 calculates and stores the square difference $W_-$ as the spin polarization degree $M_x$ whenever the artificial magnetic field A is applied, on the basis of the detection results of the polarimeter 4. The original magnetic field is then calculated using a first magnetic field (artificial magnetic field in which the magnetic field of the measurement region is set to the maximum point P) when a maximum value condition in which the square difference $W_-$ is set to a maximum value is satisfied, and a second magnetic field (artificial magnetic field in which the magnetic field of the measurement region is set to the minimum point V) when a minimum value condition in which the square difference $W_-$ is set to a minimum value is satisfied.

Figure 9:
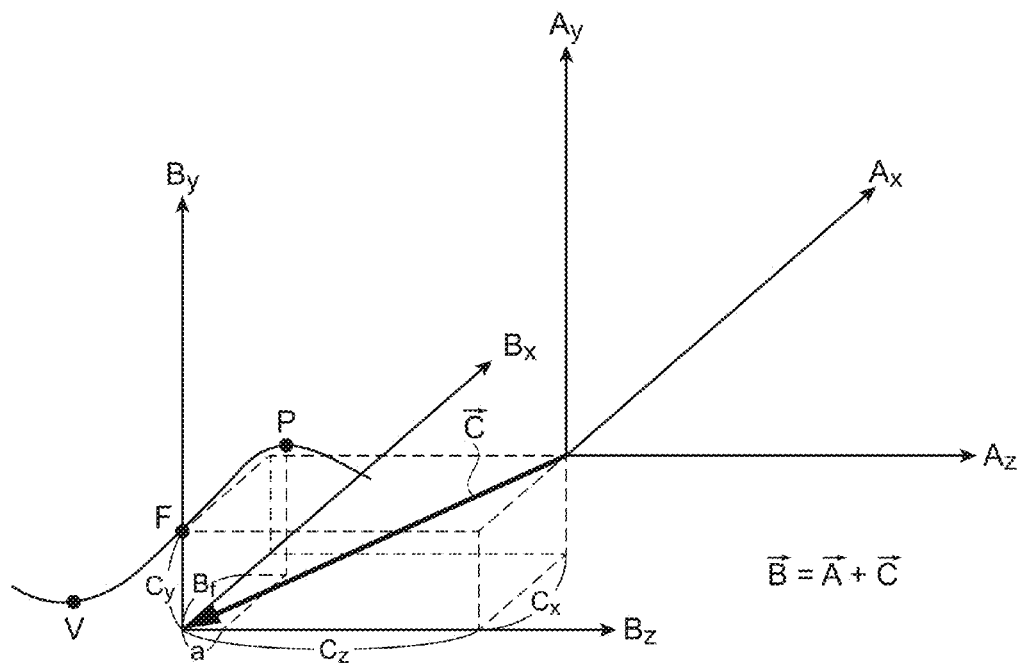
FIG. 9 is a diagram illustrating a relationship between a coordinate system of a magnetic field of a measurement region of Embodiment 1 and a coordinate system of an artificial magnetic field.

FIG. 9 is a diagram illustrating a relationship between a coordinate system of a magnetic field $B=(B_x, B_y, B_z)$ of the measurement region and a coordinate system of an artificial magnetic field $A=(A_x, A_y, A_z)$ generated by the magnetic field generator 7, when the y-axis component of the artificial magnetic field is zero ($A_y=0$). As shown in FIG. 9, the magnetic field $B=(B_x, B_y, B_z)$ of the measurement region can be calculated by performing vector addition of the artificial magnetic field $A=(A_x, A_y, A_z)$ to an original magnetic field $C=(C_x, C_y, C_z)$. A calculation expression is represented by the following Expression (22).

$$\vec{B} = \vec{A}+\vec{C} = (B_x, B_y, B_z) = (A_x + C_x, A_y + C_y, A_z + C_z) \tag{22}$$

Assuming that an artificial magnetic field when the magnetization value (spin polarization degree $M_x$) in the measurement region becomes the maximum point $P=(P_x, P_y, P_z)$ is set to the first magnetic field $A_p=(A_{px}, A_{py}, A_{pz})$, and that an artificial magnetic field when the magnetization value (spin polarization degree $M_x$) becomes the minimum point $V=(V_x, V_y, V_z)$ is set to the second magnetic field $A_v=(A_{vx}, A_{vy}, A_{vz})$, these artificial magnetic fields are represented by the following Expressions (23) and (24) from the relation of Expression (22) and a condition in which the y-axis component of the artificial magnetic field is set to a fixed value ($A_y=A_{fy}$).

$$(P_x \ P_y \ P_z) = (A_{px} + C_x \ A_{py} + C_y \ A_{pz} + C_z) \tag{23}$$
$$= (A_{px} + C_x \ A_{fy} + C_y \ A_{pz} + C_z)$$

$$(V_x \ V_y \ V_z) = (A_{vx} + C_x \ A_{vy} + C_y \ A_{vz} + C_z) \tag{24}$$
$$= (A_{vx} + C_x \ A_{fy} + C_y \ A_{vz} + C_z)$$

The midpoint F between the maximum point P and the minimum point V is deformed as in the following Expression (25) from Expression (21) and Expressions (23) and (24).

$$\vec{F} = \frac{\vec{P}+\vec{V}}{2} = \left(\frac{A_{px}+A_{vx}}{2} + C_x \ A_{fy} + C_y \ \frac{A_{pz}+A_{vz}}{2} + C_z\right) \quad (25)$$
$$= (0 \ A_{fy} + C_y \ 0)$$

Therefore, $C_x$ which is the x-axis component of the original magnetic field C can be calculated by the following Expression (26), and $C_z$ which is the z-axis component of the original magnetic field C can be calculated by the following Expression (27).

$$C_x = -\frac{A_{px}+A_{vx}}{2} \quad (26)$$

$$C_z = -\frac{A_{pz}+A_{vz}}{2} \quad (27)$$

In addition, when the x-axis component and the y-axis component are equal to each other in the maximum point P, $C_y$ which is the y-axis component of the original magnetic field C can be calculated by the following Expression (28) from the relation of $P_x=P_y$ of Expression (19) and Expression (23).

$$C_y = A_{px} + C_x - A_{fy} = \frac{A_{px}-A_{vx}}{2} - A_{fy} \quad (28)$$

Meanwhile, the y-axis component $A_y$ of the artificial magnetic field A which is generated in the measurement region may be the fixed value $A_{fy}$, and is arbitrary. When the fixed value $A_{fy}$ is zero, $C_y$ can be calculated according to the following Expression (29) at $A_{fy}=0$.

$$C_y = \frac{A_{px}-A_{vx}}{2} \quad (29)$$

In this manner, the y-axis component of the artificial magnetic field A is set to a fixed value, and a plane $A_x$–$A_y$ of $A_y=A_{fy}$ is scanned by changing the x-axis component and the z-axis component, thereby allowing the original magnetic field C to be obtained from the artificial magnetic field (first magnetic field $A_p$) in which the magnetization value (spin polarization degree $M_x$) becomes maximum and the artificial magnetic field (second magnetic field $A_v$) in which the magnetization value (spin polarization degree $M_x$) becomes minimum. As described above, since the original magnetic field C is an external magnetic field entering the magnetic shield 8, the controlling of the magnetic field generator 7 so as to offset the original magnetic field C obtained in this manner during the magnetic measurement of a measuring object such as magnetocardiogram makes it possible to reduce the adverse influence of the external magnetic field and then measure the magnetic field of the measuring object with low noise.

Flow of Processes

Figure 10:
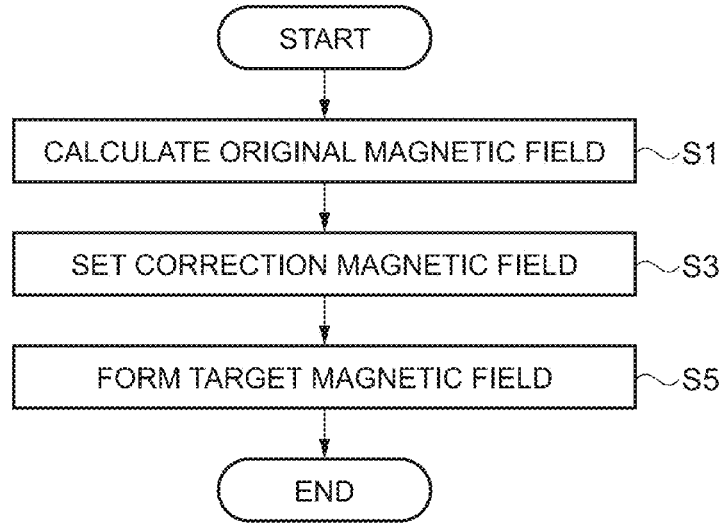
FIG. 10 is a flow diagram illustrating a procedure of a magnetic field forming process of Embodiment 1.

FIG. 10 is a flow diagram illustrating a procedure of a magnetic field forming process of Embodiment 1. The magnetic field measurement device 1 performs the magnetic field forming process shown in FIG. 10 before a subject to be tested is loaded into the magnetic shield 8 and the measurement of a biomagnetic field is performed.

As shown in FIG. 10, in the magnetic field forming process, first, the magnetic field calculation unit 53 calculates the original magnetic field C present in the measurement region (step S1). As a specific processing procedure, first, in a state where the relation of $A_y=A_{fy}$ ($A_{fy}=0$ in a preferred example) is established, the artificial magnetic field control unit 531 causes the magnetic field generator 7 to sequentially generate a plurality of artificial magnetic fields A by scanning each value of $A_x$ and $A_z$ within a predetermined range, and calculates the original magnetic field C through Expressions (26) to (28) using the first magnetic field $A_p$ when the square difference $W_-$ satisfies the maximum value condition and the second magnetic field $A_v$ when the square difference satisfies the minimum value condition. In this case, the original magnetic field C becomes an external magnetic field entering the magnetic shield 8.

Subsequently, the correction magnetic field setting unit 55 subtracts the original magnetic field C calculated in step S1 from a target magnetic field $T=(T_x, T_y, T_z)$ and sets a correction magnetic field T–C (step S3). The correction magnetic field setting unit 55 then generates the set correction magnetic field T–C in the magnetic field generator 7. Then, the original magnetic field C is offset by Expression (22) and the target magnetic field T is formed in the measurement region (step S5). In the present embodiment, as an example, the correction magnetic field T–C=–C is set as the target magnetic field T=(0, 0, 0), and a zero magnetic field is formed in the measurement region. In this manner, in a state where the target magnetic field such as the zero magnetic field is formed in the measurement region (that is, in a state where the correction magnetic field T–C is generated in the measurement region), a minute magnetic field (magnetocardiogram or magnetoencephalo) which is emitted from a measuring object (for example, person) disposed in the measurement region is measured. Since the target magnetic field is formed in the measurement region, it is possible to measure a minute magnetic field with a high degree of accuracy.

As described above, according to the present embodiment, it is possible to calculate the original magnetic field C present in the measurement region. In addition, the zero magnetic field is formed by offsetting the original magnetic field C in the measurement region, and the subject to be tested is load thereon into the magnetic shield 8, thereby allowing the measurement of a biomagnetic field to be performed. According to this, it is possible to measure the biomagnetic field with good sensitivity and with a high degree of accuracy.

Embodiment 2

In the aforementioned Embodiment 1, in a state where the y-axis component $A_y$ is set to the fixed value $A_{fy}$ (for example, zero), a plurality of artificial magnetic fields A are generated by changing the x-axis component $A_x$ and the z-axis component $A_z$. On the other hand, in the present embodiment, in a state where the x-axis component $A_x$ is set to the fixed value $A_{fx}$ (for example, zero), a plurality of artificial magnetic fields A may be generated by changing the y-axis component $A_y$ and the z-axis component $A_z$. The original magnetic field $C=(C_x, C_y, C_z)$ may be calculated by the following Expressions (30) to (32) using the first magnetic field $A_p=(A_{fx}, A_{py}, A_{pz})$ when the square difference $W_-$ satisfies the maximum value condition and the second magnetic field $A_v=(A_{fx}, A_{vy}, A_{vz})$ when the square difference $W_-$ satisfies the minimum value condition in which a minimum value is set.

$$C_x = -\frac{A_{py} + A_{vy}}{2} - A_{fx} \qquad (30)$$

$$C_y = \frac{A_{py} - A_{vy}}{2} \qquad (31)$$

$$C_z = -\frac{A_{pz} + A_{vz}}{2} \qquad (32)$$

A method to obtain Expression (30) to Expression (32) is the same as that in Embodiment 1.

In the magnetic field measurement method (how to calculate the original magnetic field C) of the present embodiment, the same operational effect as that in the above Embodiment 1 is also obtained.

Embodiment 3

Next, a magnetic field measurement device of Embodiment 3 and a magnetic field measurement method using the device will be described with reference to FIGS. 11 to 15.

Entire Configuration

First, the magnetic field measurement device of the present embodiment will be described with reference to FIG. 11.

Figure 11:
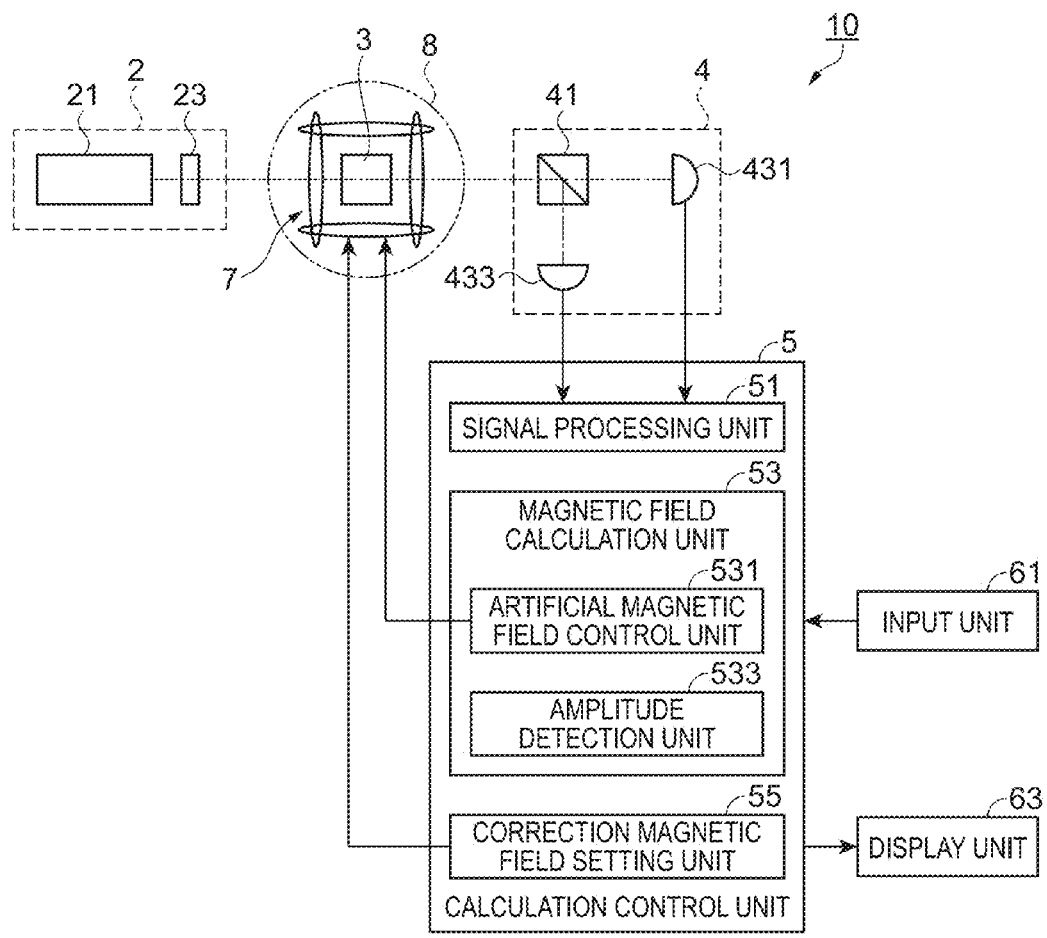
FIG. 11 is a diagram illustrating an entire configuration example of a magnetic field measurement device of Embodiment 3.

FIG. 11 is a diagram illustrating an entire configuration example of a magnetic field measurement device of Embodiment 3.

As shown in FIG. 11, a magnetic field measurement device 10 of the present embodiment has substantially the same configuration as that of the magnetic field measurement device 1 of the above Embodiment 1. The magnetic field calculation unit 53 of the calculation control unit 5 includes an amplitude detection unit 533 in addition to the artificial magnetic field control unit 531. Therefore, the same components as those of the magnetic field measurement device 1 of Embodiment 1 are denoted by the same reference numerals and signs, and thus the detailed description thereof will not be given. Hereinafter, components having different configurations will be described.

The artificial magnetic field control unit 531 controls the magnetic field generator 7, and sequentially generates, in the measurement region, artificial magnetic fields of a plurality of combinations obtained by changing an artificial magnetic field component in each axial direction of the x-axis, the y-axis, and the z-axis, that is, artificial magnetic fields obtained by periodically changing the z-axis component by superimposing a predetermined alternating-current component on the artificial magnetic field component (referred to as the z-axis component) in the z-axis direction. The amplitude detection unit 533 detects the ratio of the temporal change of the square difference $W_-$ to the temporal change of the z-axis component by extracting an amplitude and a phase from the temporal change of the square difference $W_-$ as an example of a value corresponding to the magnetization value calculated by the signal processing unit 51. The amplitude detection unit 533 can be configured using a lock-in amplifier or the like.

How to calculate the original magnetic field C in the calculation control unit 5 of the present embodiment, that is, a magnetic field measurement method is different from that in Embodiment 1 or Embodiment 2.

The magnetic field measurement method of the present embodiment is to obtain the original magnetic field C with a focus on a differential value $\partial M_x/\partial B_z$ obtained by differentiating, by $B_z$, the spin polarization degree $M_x$ as a magnetization value which is the x-axis component (component in the first direction) of the magnetization vector of the medium (gaseous atoms) in the gas cell 3.

Specifically, the differential value $\partial M_x/\partial B_z$ obtained by differentiating the spin polarization degree $M_x$ of Expression (14) by $B_z$ is represented by the following Expression (33).

$$\frac{\partial M_x}{\partial B_z} = \left(\frac{c}{a}\right)\frac{a(a^2 + B_x^2 + B_y^2 - B_z^2) - 2 B_x B_y B_z}{(a^2 + B_x^2 + B_y^2 + B_z^2)^2} \qquad (33)$$

The differential value $\partial M_x/\partial B_z$ represented by Expression (33) shows a change in output (spin polarization degree $M_x$) with respect to a change in the amount of detection (z component $B_z$ of a magnetic field), and thus means detection sensitivity. That is, in a condition in which the differential value $\partial M_x/\partial B_z$ becomes maximum, the measurement sensitivity of the magnetic field measurement device 10 becomes maximum. Even when $B_x$ or $B_y$ has a certain value, the denominator of Expression (33) increases by the fourth power of these values. On the other hand, the numerator of Expression (33) changes at the square of $B_x$ or $B_y$, and thus the differential value $\partial M_x/\partial B_z$ becomes maximum when $B_x=B_y=0$ with respect to $B_x$ and $B_y$. The differential value $\partial M_x/\partial B_z$ in this case is represented by the following Expression (34).

$$\frac{\partial M_x}{\partial B_z} = \frac{c(a^2 - B_z^2)}{(a^2 + B_z^2)^2} \qquad (34)$$

Figure 12:
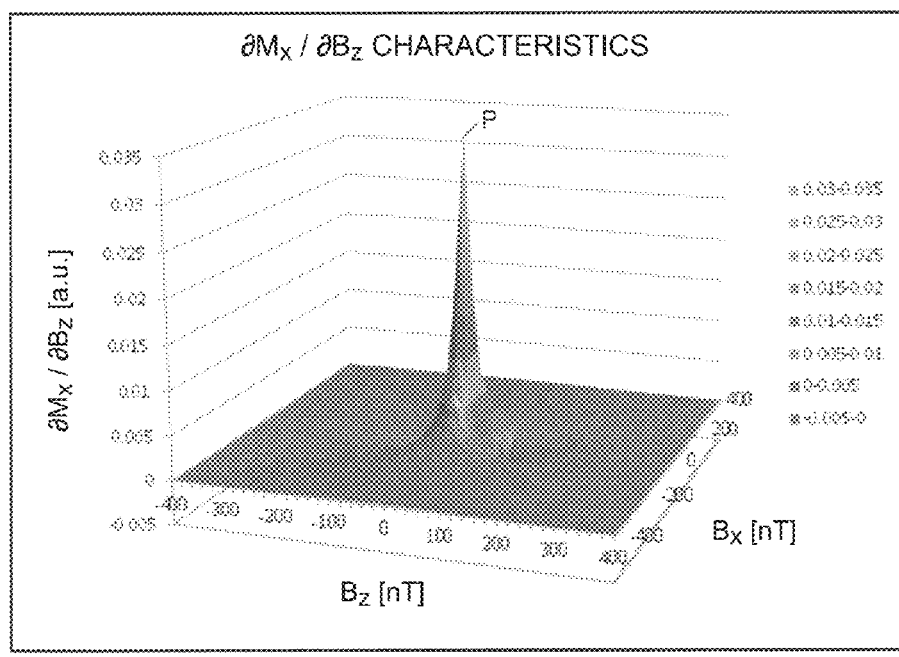
FIG. 12 is a diagram illustrating a three-dimensional distribution relating to $B_x$ and $B_z$ of a differential value $\partial M_x/\partial B_z$.
Figure 13:
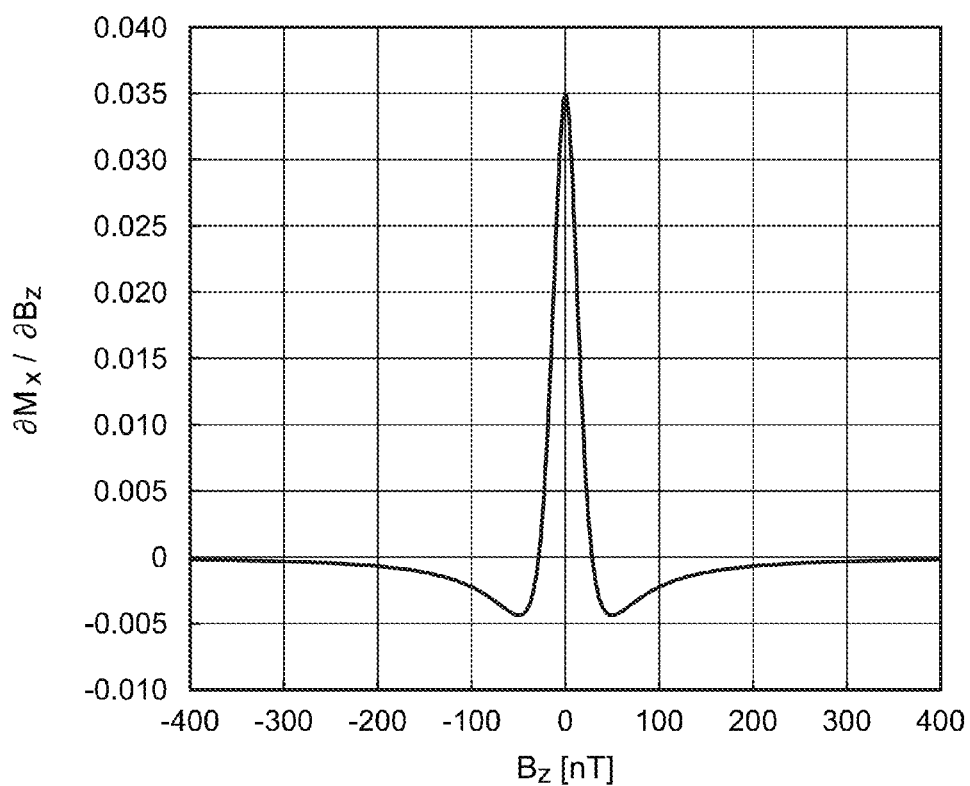
FIG. 13 is a diagram illustrating a two-dimensional distribution relating to $B_z$ of the differential value $\partial M_x/\partial B_z$ when $B_x=0$.

FIG. 12 is a diagram illustrating a three-dimensional distribution relating to $B_x$ and $B_z$ of the differential value $\partial M_x/\partial B_z$, and FIG. 13 is a diagram illustrating a two-dimensional distribution relating to $B_z$ of the differential value $\partial M_x/\partial B_z$ when $B_x=0$.

When each value of $B_x$ and $B_z$ is changed at $B_y=0[\text{nT}]$, a result as shown in FIG. 12 is obtained. Alternatively, when each value of $B_z$ is changed at $B_x=B_y=0$ [nT], a result as shown in FIG. 13 is obtained. As shown in FIGS. 12 and 13, one maximum value appears in the distribution of the differential value $\partial M_x/\partial B_z$ and the differential value $\partial M_x/\partial B_z$ becomes maximum when $B_z=0$ in a case of $B_x=B_y=0$. Therefore, when the measurement region is a zero magnetic field (each value of $B_x$, $B_y$, and $B_z$ is zero), a change in the spin polarization degree $M_x$ (that is, square difference $W_-$) with respect to a change in magnetic field along the z-axis direction (direction of travel of the probe light) becomes maximum, and sensitivity becomes maximum. In other words, in order to minimize the original magnetic field such as an external magnetic field in the measurement region, the artificial magnetic field may be adjusted so that the differential value $\partial M_x/\partial B_z$ becomes maximum.

Here, the differential value $\partial M_x/\partial B_z$ (ratio of the temporal change of the spin polarization degree $M_x$ to the temporal change of $B_z$) can be replaced by the ratio of the temporal change of the square difference $W_-$ to the temporal change of $B_z$. Consequently, in the magnetic field forming process of the present embodiment, artificial magnetic fields of a plurality of combinations obtained by changing the x-axis component, the y-axis component, and the z-axis component, that is, artificial magnetic fields obtained by periodically changing the z-axis component are sequentially generated in the measurement region, and an artificial magnetic field in which the differential value $\partial M_x/\partial B_z$ which is a ratio of the temporal change of the spin polarization degree $M_x$ to the temporal change of the $B_z$ becomes maximum is searched for. In this case, it is preferable that the angular frequency ω of the z-axis component is set to a value equal to or less than a cut-off angular frequency $ω_C$. The cut-off angular frequency $ω_C$ is a sum of the relaxation rate $Γ_0$ of the spin polarization degree $M_x$ and the optical pumping rate $Γ_p$ ($ω_C=Γ_0+Γ_p$), and is approximately 100 Hz in the present embodiment. That is, it is preferable that the z-axis component of the artificial magnetic field satisfies a relation of $ω<ω_C=Γ_0+Γ_p$, and the angular frequency ω is equal to or less than 100 Hz in the present embodiment. When the angular frequency ω of the z-axis component is set to a value equal to or less than the cut-off angular frequency $ω_C$, $dM_x/dt$ can be regarded as approximately zero, and the approximation of the left-hand side of Expression (11) to be zero is justified. That is, when the relation of $ω<ω_C=Γ_0+Γ_p$ is satisfied, the original magnetic field C present in the measurement region can be accurately measured. However, since the magnetic field measurement device 10 acts like a primary low-pass filter, a gain and a phase in the vicinity of the cut-off angle frequency $ω_C$ gently decreases with an increase in angular frequency ω. For this reason, the angular frequency ω of a periodic function which is superimposed in reality may be made larger by approximately 10 percent than the cut-off angular frequency $ω_C$.

As a specific measurement method, the x-axis component $A_x$ and the y-axis component $A_y$ of the artificial magnetic field are set to a fixed magnetic field, and a magnetic field represented by a periodic function is applied to the z-axis component, to thereby measure a ratio of the temporal change of the spin polarization degree $M_x$ to the temporal change of $B_z$. This is measured at various levels, and an artificial magnetic field in which the differential value $∂M_x/∂B_z$ becomes maximum is specified. For example, as a first measurement, $A_x=0$, $A_y=0$, and $A_z$ are set to a vibration magnetic field around 0 (as an example, $A_z=\sin ωt$), and a first differential value $∂M_x/∂B_z$ is measured. Next, as a second measurement, $A_x=0$, $A_y=0$, and $A_z$ are set to a vibration magnetic field around 1 (as an example, $A_z=1+\sin ωt$), and a second differential value $∂M_x/∂B_z$ is measured. Next, as a third measurement, $A_x=0$, $A_y=0$, and $A_z$ are set to a vibration magnetic field around −1 (as an example, $A_z=-1+\sin ωt$), and a third differential value $∂M_x/∂B_z$ is measured. Next, as a fourth measurement, $A_x=0$, $A_y=1$, and $A_z$ are set to a vibration magnetic field around 0 (as an example, $A_z=\sin ωt$), and a fourth differential value $∂M_x/∂B_z$ is measured. Next, as a fifth measurement, $A_x=0$, $A_y=1$, and $A_z$ are set to a vibration magnetic field around 1 (as an example, $A_z=1+\sin ωt$), and a fifth differential value $∂M_x/∂B_z$ is measured. Next, as a sixth measurement, $A_x=0$, $A_y=1$, and $A_z$ are set to a vibration magnetic field around −1 (as an example, $A_z=-1+\sin ωt$), and a sixth differential value $∂M_x/∂B_z$ is measured. Next, as a seventh measurement, $A_x=0$, $A_y=-1$, and $A_z$ are set to a vibration magnetic field around 0 (as an example, $A_z=\sin ωt$), and a seventh differential value $∂M_x/∂B_z$ is measured. Next, as an eighth measurement, $A_x=0$, $A_y=-1$, and $A_z$ are set to a vibration magnetic field around 1 (as an example, $A_z=1+\sin ωt$), and an eighth differential value $∂M_x/∂B_z$ is measured. Next, as a ninth measurement, $A_x=0$, $A_y=-1$, and $A_z$ are set to a vibration magnetic field around −1 (as an example, $A_z=-1+\sin ωt$), and a ninth differential value $∂M_x/∂B_z$ is measured. In this manner, a lot of measurements are repeated centering on $A_y=0$, an artificial magnetic field in which the differential value $∂M_x/∂B_z$ becomes maximum is specified from a lot of differential values $∂M_x/∂B_z$ obtained in this manner. In other words, the differential value $∂M_x/∂B_z$ is detected by extracting an amplitude from the period change of the square difference $W_-$ calculated by the signal processing unit 51, on the basis of the detection results of the polarimeter 4, for each of a plurality of artificial magnetic fields of each combination. The original magnetic field C is calculated using an artificial magnetic field when a condition for external value in which the differential value $∂M_x/∂B_z$ is set to a maximum value is satisfied. A process of obtaining the maximum value of the differential value $∂M_x/∂B_z$ while changing the artificial magnetic field can be realized using publicly known optimization processing. As described above, in order to search for an artificial magnetic field in which the differential value $∂M_x/∂B_z$ becomes maximum, making a search for the y-axis component $A_y$ of the artificial magnetic field from the vicinity of zero is preferable from the aspect of efficiency.

Figure 14:
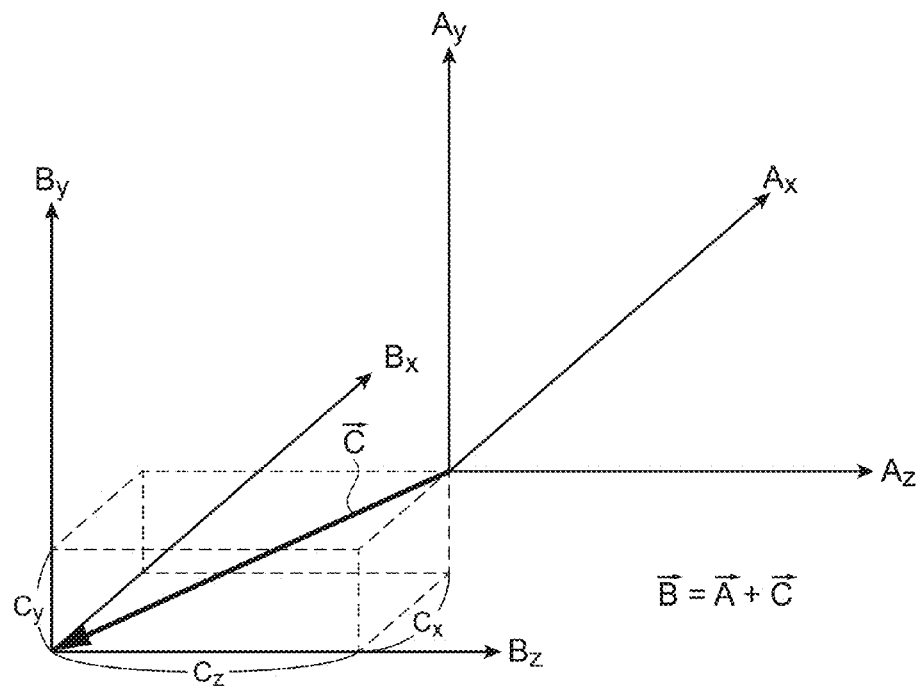
FIG. 14 is a diagram illustrating a relationship between a coordinate system of a magnetic field of a measurement region of Embodiment 3 and a coordinate system of an artificial magnetic field.

FIG. 14 is a diagram illustrating a relationship between a coordinate system of a magnetic field $B=(B_x, B_y, B_z)$ of the measurement region and a coordinate system of an artificial magnetic field $A=(A_x, A_y, A_z)$ generated by the magnetic field generator 7, in the present embodiment. As shown in FIG. 14, each component of the magnetic field $B=(B_x, B_y, B_z)$ of the measurement region can be calculated by performing vector addition of each component of the artificial magnetic field $A=(A_x, A_y, A_z)$ to the original magnetic field $C=(C_x, C_y, C_z)$. A calculation expression is represented by the following Expression (35).

$$\vec{B}=\vec{A}+\vec{C}=(B_x,B_y,B_z)=(A_x+C_x,A_y+C_y,A_z+C_z) \quad (35)$$

As described above, the magnetic field of the measurement region when the condition for external value in which the differential value $∂M_x/∂B_z$ is set to a maximum value is satisfied, that is, when the extracted amplitude becomes maximum is a zero magnetic field (B=0), and thus the original magnetic field C ($C_x, C_y, C_z$) is represented by the following Expressions (36) to (38), using an artificial magnetic field $A_h$ ($A_{hx}, A_{hy}, A_{hz}$) when the condition for external value is satisfied, from the relation of Expression (35).

$$C_x=-A_{hx} \quad (36)$$

$$C_y=-A_{hy} \quad (37)$$

$$C_z=-A_{hz} \quad (38)$$

Flow of Processes

Figure 15:
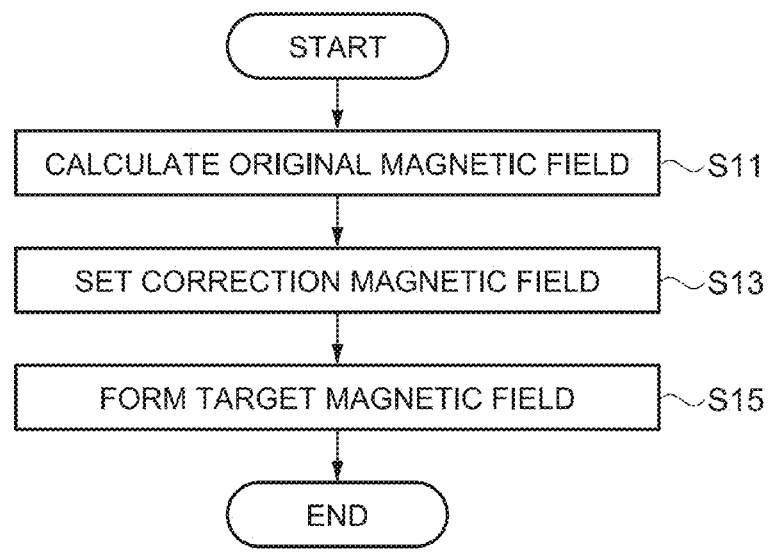
FIG. 15 is a flow diagram illustrating a procedure of a magnetic field forming process of Embodiment 3.

FIG. 15 is a flow diagram illustrating a procedure of a magnetic field forming process in the present embodiment. The magnetic field measurement device 10 performs the magnetic field forming process shown in FIG. 15 before a subject to be tested is loaded into the magnetic shield 8 and the measurement of a biomagnetic field is performed.

As shown in FIG. 15, in the magnetic field forming process, first, the magnetic field calculation unit 53 calculates the original magnetic field C present in the measurement region (step S11). As a specific processing procedure, first, the artificial magnetic field control unit 531 sequentially generates the above-mentioned artificial magnetic fields of a plurality of combinations in the measurement region through the magnetic field generator 7, and the amplitude detection unit 533 extracts the amplitude of the square difference $W_-$ which is obtained as measurement results every time. The magnetic field calculation unit 53 then calculates the original magnetic field C by Expressions (36) to (38) using the artificial magnetic field $A_h$ when the amplitude of the square difference $W_-$ becomes maximum.

Subsequently, the correction magnetic field setting unit 55 sets the correction magnetic field T-C by subtracting the original magnetic field C calculated in step S11 from the target magnetic field T ($T_x, T_y, T_z$) (step S13). The correction magnetic field setting unit 55 then generates the set correction magnetic field T−C in the magnetic field generator 7, and thus forms the target magnetic field T in the measurement region by offsetting the original magnetic field C (step S15). In the present embodiment, as an example, the correction magnetic field T−C is set as the target magnetic field T=(0, 0, 0), and a zero magnetic field is formed in the measurement region.

As described above, according to the present embodiment, it is possible to calculate the original magnetic field C present in the measurement region. In addition, the zero magnetic field is formed by offsetting the original magnetic field C in the measurement region, and the subject to be tested is load thereon into the magnetic shield 8, thereby allowing the measurement of a biomagnetic field to be performed. According to this, it is possible to measure the biomagnetic field with good sensitivity and with a high degree of accuracy.

A basic technical idea common to the magnetic field measurement methods of Embodiment 1 to the above Embodiment 3 has a technical feature in which there is provided a magnetic field measurement method of measuring a magnetic field of a measurement region in a magnetic field measurement device including a light source unit that emits linearly polarized light in which a first direction (x-axis direction), a second direction (y-axis direction) and a third direction (z-axis direction) are orthogonal to each other, a gas cell having a medium filled therein, which is disposed in the measurement region, which changes optical characteristics of the linearly polarized light in accordance with a magnetic field, and which is irradiated along the third direction (z-axis direction) with the linearly polarized light of which a vibration direction of an electric field is the second direction (y-axis direction), an optical detector that detects the optical characteristics, and a magnetic field generator that applies an artificial magnetic field to the measurement region, the method including generating a plurality of artificial magnetic fields, obtained by changing an artificial magnetic field component in the third direction (z-axis direction), in the magnetic field generator, calculating a magnetization value which is a component of a magnetization vector of the medium in the first direction or a value corresponding to the magnetization value on the basis of detection results of the optical detector, and calculating an original magnetic field C present in the measurement region, using an artificial magnetic field when the magnetization value or the value corresponding to the magnetization value satisfies a specified condition.

MODIFICATION EXAMPLE

In addition, in the aforementioned embodiment, the gas cell 3 having alkali metal atoms sealed in a gaseous state is used as a medium for generating polarization in a magnetic moment and rotating the plane of polarization of transmitted light in accordance with the intensity of a magnetic field, but a medium other than the alkali metal atoms may be used. For example, a solid-state element such as a diamond providing a lattice defect due to nitrogen may be used as a medium. In addition, the magnetic field measurement method and the magnetic field measurement device according to various embodiments of the invention can also be applied to an atomic oscillator using a small gas cell of a millimeter size, in addition to a magnetic sensor.

In addition, the embodiment in which the target magnetic field is set to a zero magnetic field has been described, but the target magnetic field can be set to any magnetic field other than the zero magnetic field.

What is claimed is:

1. A magnetic field measurement method of measuring a magnetic field of a measurement region in a magnetic field measurement device, the magnetic field measurement device including (i) a light source unit that emits linearly polarized light in which a first direction, a second direction and a third direction are orthogonal to each other, (ii) a medium, disposed in the measurement region, which changes optical characteristics of the linearly polarized light in accordance with a magnetic field, and that is irradiated along the third direction with the linearly polarized light of which a vibration direction of an electric field of the linearly polarized light is the second direction, (iii) an optical detector that detects the optical characteristics, and (iv) a magnetic field generator that applies an artificial magnetic field to the measurement region, the method comprising:

generating and applying to the measurement region a plurality of artificial magnetic fields, obtained by changing an artificial magnetic field component in the third direction and one artificial magnetic field component in the first direction and the second direction, in the magnetic field generator, in a state where the other artificial magnetic field component in the first direction and the second direction is set to a fixed value in each of the plurality of artificial magnetic fields;

calculating a magnetization value that is a component of a magnetization vector of the medium in the first direction or a value corresponding to the magnetization value based on detection results of the optical detector for each of the plurality of artificial magnetic fields; and calculating an original magnetic field present in the measurement region, based on a selected artificial magnetic field of the plurality of artificial magnetic fields when the magnetization value in the selected artificial magnetic field or the value corresponding to the magnetization value in the selected artificial magnetic field satisfies a condition for external value.

2. The magnetic field measurement method according to claim 1, wherein the calculating of the original magnetic field includes calculating using:

a first magnetic field that is an artificial magnetic field when the magnetization value or value corresponding to the magnetization value satisfies a maximum value condition; and a second magnetic field that is an artificial magnetic field when the magnetization value or value corresponding to the magnetization value satisfies a minimum value condition.

3. The magnetic field measurement method according to claim 2, wherein the one artificial magnetic field component is an artificial magnetic field component in the first direction, and the other artificial magnetic field component is an artificial magnetic field component in the second direction, and the calculating of the original magnetic field includes calculating using the following Expressions (4) to (6):

$$C_x = -\frac{A_{py} + A_{vy}}{2} - A_{fx} \quad (4)$$

$$C_y = \frac{A_{py} - A_{vy}}{2} \quad (5)$$

-continued $$C_z = -\frac{A_{pz} + A_{vz}}{2} \quad (6)$$

where, $A_{py}$ is a component of the first magnetic field in the second direction, $A_{vy}$ is a component of the second magnetic field in the second direction, $A_{pz}$ is a component of the first magnetic field in the third direction, $A_{vz}$ is a component of the second magnetic field in the third direction, $A_{fx}$ is the fixed value, $C_x$ is a component of the original magnetic field in the first direction, $C_y$ is a component of the original magnetic field in the second direction, and $C_z$ is a component of the original magnetic field in the third direction.

4. The magnetic field measurement method according to claim 1, wherein the one artificial magnetic field component is an artificial magnetic field component in the second direction, and the other artificial magnetic field component is an artificial magnetic field component in the first direction, and the calculating of the original magnetic field includes calculating using the following Expressions (1) to (3):

$$C_x = -\frac{A_{px} + A_{vx}}{2} \quad (1)$$

$$C_y = \frac{A_{px} - A_{vx}}{2} - A_{fy} \quad (2)$$

$$C_z = \frac{A_{pz} + A_{vz}}{2} \quad (3)$$

where, $A_{px}$ is a component of the first magnetic field in the first direction, $A_{vx}$, is a component of the second magnetic field in the first direction, $A_{pz}$ is a component of the first magnetic field in the third direction, $A_{vz}$ is a component of the second magnetic field in the third direction, $A_{fy}$, is the fixed value, $C_x$ is a component of the original magnetic field in the first direction, $C_y$ is a component of the original magnetic field in the second direction, and $C_z$ is a component of the original magnetic field in the third direction.

5. The magnetic field measurement method according to claim 1, wherein the fixed value is zero.

6. The magnetic field measurement method according to claim 1, further comprising:

generating a magnetic field of a difference in the original magnetic field with respect to a target magnetic field, in the magnetic field generator;

disposing a measuring object in the measurement region; and measuring a magnetic field which is radiated by the measuring object, using the detection results of the optical detector while the magnetic field of the difference is generated.

* * * * *